(12) United States Patent  (10) Patent No.: US 8,438,928 B2
Frederick et al.  (45) Date of Patent: May 14, 2013

(54) APPARATUS AND METHOD FOR NON-DESTRUCTIVE TESTING USING ULTRASONIC PHASED ARRAY

(75) Inventors: Caleb Frederick, Cornelius, NC (US); Allen Porter, Huntersville, NC (US)

(73) Assignee: Structural Integrity Associates, Inc., Huntersville, NC (US)

( * ) Notice: Subject to any disclaimer, the term of this patent is extended or adjusted under 35 U.S.C. 154(b) by 319 days.

(21) Appl. No.: 12/781,097

(22) Filed: May 17, 2010

(65) Prior Publication Data

US 2011/0277549 A1  Nov. 17, 2011

(51) Int. Cl.
*G01N 29/02* (2006.01)

(52) U.S. Cl.
USPC ............................................... 73/627; 73/644

(58) Field of Classification Search .................... 73/627, 73/628, 641, 644
See application file for complete search history.

(56) References Cited

U.S. PATENT DOCUMENTS

| | | | | |
|---|---|---|---|---|
| 2,874,568 | A | * | 2/1959 | Petermann ................. 73/861.02 |
| 4,821,838 | A | * | 4/1989 | Chen ............................ 181/175 |
| 5,431,054 | A | | 7/1995 | Reeves et al. |
| 5,466,019 | A | * | 11/1995 | Komolrochanaporn ...... 285/343 |
| 6,082,198 | A | * | 7/2000 | Sabourin et al. ................ 73/633 |
| 6,736,011 | B2 | | 5/2004 | Zayicek et al. |
| 6,789,427 | B2 | | 9/2004 | Batzinger et al. |
| 6,813,950 | B2 | | 11/2004 | Glascock et al. |
| 7,328,619 | B2 | | 2/2008 | Moles et al. |
| 7,428,842 | B2 | | 9/2008 | Fair et al. |
| 7,624,651 | B2 | | 12/2009 | Fernald et al. |
| 7,694,569 | B2 | * | 4/2010 | McGrath et al. ................ 73/644 |
| 7,984,650 | B2 | * | 7/2011 | Brignac .......................... 73/618 |
| 8,087,298 | B1 | * | 1/2012 | DiMambro et al. ............ 73/629 |
| 8,150,652 | B2 | * | 4/2012 | Rager et al. ................... 702/159 |
| 8,166,823 | B2 | * | 5/2012 | Lam et al. ........................ 73/622 |
| 2009/0277270 | A1 | * | 11/2009 | Huebler et al. ................. 73/622 |

OTHER PUBLICATIONS

I. J. Munns and G. A. Georgiou; Ultrasonic and Radiographic NDT or Butt Fusion Welds in Polyethylene Pipe—Paper presented at Plastic Pipes IX Heriot-Watt University, Edinburgh, Scotland, UH, Sep. 18-21, 1995.

* cited by examiner

*Primary Examiner* — J M Saint Surin
(74) *Attorney, Agent, or Firm* — Clements Bernard PLLC; Seth L. Hudson

(57) ABSTRACT

The present invention is related generally to the field of non-destructive materials testing using ultrasonic devices, more particularly, ultrasonic devices in a phased array and includes a wedge for conducting pitch-catch ultrasonic phase array testing of materials wherein the wedge includes a liquid column and is manufactured with specific angles so as to control the angle at which the ultrasonic waves pass into the wedge and then are refracted when passing from the liquid in the liquid column into the material being analyzed, thus providing a wider range of analysis via sweeping the beams from the wedge than was possible with known wedges.

5 Claims, 7 Drawing Sheets

APPARATUS AND METHOD FOR NON-DESTRUCTIVE TESTING USING ULTRASONIC PHASED ARRAY

FIELD OF THE INVENTION

The present invention is related generally to the field of non-destructive materials testing using ultrasonic devices, more particularly, ultrasonic devices in a phased array. The present invention relates to a novel wedge design for conducting pitch-catch ultrasonic phase array testing of materials. More specifically, the present invention relates to an apparatus and method to non-destructively and volumetrically examine butt-fusion joints in high-density polyethylene using liquid to achieve refraction of the ultrasonic waves.

CROSS-REFERENCE TO RELATED APPLICATION

Not Applicable

BACKGROUND OF INVENTION

As buildings, municipal piping systems, and industrial facilities continue to grow in both size and capacity, the need to verify that the components used to build these systems are working properly and free from defects will continue to rise. Due to the nature of the structural components, it is simply not possible to test each and every element prior to its use. Thus, a need exists for a way to test the components in these structures without destroying the structure during the testing. Non-destructive testing allows for one to test these structures and components while they are being used or after they are already part of a structure without harm to the component or structure. The term "non-destructive testing" (NDT) refers to a diverse group of analysis techniques used in the sciences and in industry to evaluate the properties of a material, component or system without causing damage to the material, component or system as a result of the testing. The value of such testing methods is easily appreciated, because the item being analyzed could be expensive or already part of a larger structure. Thus, non-destructive testing is a highly valuable technique that can save both money and time in product evaluation, troubleshooting, and research.

Because non-destructive testing methods are advantageous, many different techniques for conducting non-destructive testing have been developed. Some of the more common methods include ultrasonic, magnetic-particle, liquid penetrant, radiographic, and eddy-current testing. These various methods provide a means for evaluating materials that is useful to many industries including forensic engineering, mechanical engineering, electrical engineering, civil engineering, systems engineering, medicine, nuclear regulation, and others.

Of these various methods of non-destructive testing, perhaps one of the most widely used is ultrasonic testing. In ultrasonic testing, very short ultrasonic pulse-waves with center frequencies ranging from 0.1-15 MHz and occasionally up to 50 MHz are launched into materials to detect internal flaws or to characterize materials. Ultrasonic testing is also commonly used to determine the thickness of the test object, particularly when it would be impossible to determine the thickness of a material without breaking it open. An example of this is the testing of pipes. Ultrasonic testing is often used to measure the thickness of pipes that are part of a piping system and may have suffered from corrosion. Without a non-destructive testing method, the pipe would have to be removed from the pipe system and checked for corrosion. Obviously this would be time consuming, expensive, and potentially lead to further problems with removing and replacing certain sections of pipe. Use of a non-destructive technique such as ultrasonic testing allows one to evaluate and analyze the pipe without removing it from the system or breaking it open. The ultrasonic testing can determine the pipe thickness and this information can disclose whether the pipe is suffering corrosion and, indeed, to what extent it has already corroded.

Ultrasonic testing is basically a way to pass sound waves through a structure and measure the waves reflection or diffraction as they pass through the material comprising the structure. In ultrasonic testing, an ultrasound transducer connected to a diagnostic machine is passed over the object being inspected. The transducer, which is responsible for sending out the sound waves, is typically separated from the test object by a thin barrier called a "couplant." Typically the couplant of choice is gel, oil, or water, as in immersion testing.

Ultrasonic testing usually involves one of two methods of receiving the ultrasound waveform, reflection or diffraction. In a reflection configuration (typically referred to as "pulse-echo") the transducer performs both the sending and the receiving of the ultrasonic sound waves as the sound or wave is reflected back to the transducer from which it originated. As the ultrasonic sound waves pass through the material or object, any change in the consistency of the material or object will cause a reflection of the wave. Reflected ultrasound, therefore, results whenever a wave comes into contact with an imperfection in the material. In addition, like an imperfection within the material, the "back wall" (back surface) of the material will also cause a reflection of the ultrasonic waves. This is due to the transition from the material to either air or whatever material is on the other side of the material being analyzed. Thus, the back wall of a pipe will cause a reflection of the ultrasonic sound waves. The transducer that sent out the ultrasonic sound waves is configured to receive the reflected waves from the broadcasted ultrasonic waves. In essence, the transducer listens for the echo from the reflected ultrasonic waves In contrast to a pulse echo setup, ultrasonic testing also can employ a through-transmission setup. In a through-transmission setup, the transducer broadcasts an ultrasonic wave through the material being tested, and a separate receiver on the other side of the material detects the signal. The separate receiver listens for the ultrasonic waves and records the waves as they complete passage through the material being tested. Like the pulse-echo setup, the amount and timing of ultrasonic waves that reach the receiver after traveling through the material will indicate severity and location of imperfections or other conditions in the material being tested. Any space or imperfections between the transmitter and receiver will reduce the amount of sound waves that pass through, thus revealing the presence of the imperfection or transition.

Typically, the transducer is coupled with a monitoring system or printer such that the instrument can display the results in the form of a signal with a distinct amplitude. The amplitude of the signal, represented by peak height, represents the intensity of the reflected sound wave. The distance between the peaks is typically proportional to and represents the distance between the surface of the material being analyzed and the imperfection, flaw, back wall, geometry, or other obstruction that caused the reflection of the ultrasonic wave. This distance is directly proportional to the arrival time of the reflection.

Of particular interest to the instant application is the method of ultrasonic non-destructive testing using a phased array. In a phased array, multiple transducers are used to generate a plurality of ultrasonic pulses. These ultrasonic pulses can be steered by varying the time delay at which the ultrasonic wave is pulsed. These delays are applied during emission and reception of the ultrasonic signals. By varying the time the waves are pulsed, the resultant wave front can be steered. This results in the ability to focus the beam and scan a larger area from a fixed position due to the ability to sweep the beam by varying the time delay in the phased array.

Unlike a phased array, a conventional probe is able to obtain a fixed beam angle by using an angled wedge. The obtained angle of refraction is defined by the wedge angle and the propagation speed in the wedge and in the inspected material (Snell's law). Due to the time delay introduced by the wedge, the time of emission (at the interface) is different. The waves generated from the shortest wedge path will start to propagate into the material sooner, while these generated from the longest wedge path will start entering the material later. At a specific point in the material, all the waves will be in phase (focused) and will continue propagating into the material while creating a wave front. The wave front travels into the material at a given angle (angle of refraction) following the delays that occur at the interface level. If the wedge angle or the propagation velocity of the wedge is changed, the delays are different and consequently a beam with another angle of refraction will be generated. Thus, one can steer the beam and control where the beam is focused.

Use of ultrasonic non-destructive testing to analyze materials is well known in the prior art. Ultrasonic transducers which have been used in pulse-echo mode to locate flaws and defects in tubular goods are well known. In the pulse-echo mode, the ultrasonic transducer emits an ultrasonic wave and then waits to receive an echo from the defect. The angle of incidence and angle of reflection relative to the surface of the defect must be approximately equal. As a result, a transmitting transducer can only receive an echo from the defect surface which is approximately normal to the direction of ultrasonic wave transmission. If the defect surface is more than about five degrees off-normal to the direction of propagation, the ultrasonic wave will be reflected but will not return optimal acoustic energy to the transmitting transducer for the defect to be detected.

Ultrasonic transducers have also been used in the past in pulse-echo mode to generate ultrasonic shear waves which travel circumferentially around the tubular goods being examined, and to detect axially-oriented flaws. Axially oriented ultrasonic transducers have also been used to generate axial shear waves and to detect circumferentially-oriented flaws. For some purposes, ultrasonic transducers have been oriented perpendicular to the examined surface, for instance to determine wall thickness, and have been operated in a pulse-echo mode.

Utilizing separate transmitting and receiving transducers is commonly referred to as a pitch-catch configuration. Each transducer commonly comprises a piezoelectric element and is mounted in a block of suitable material to form a search unit. Upon receipt of an electronic signal, each piezoelectric element transmits an ultrasonic signal into the material with which the search unit is in acoustical contact. Conversely, upon receipt of a suitable ultrasonic signal from the material, each piezoelectric element produces an electric signal proportional to the pressure amplitude of the ultrasonic signal incident on the element. The amplitude and shape of the voltage signal produced upon receipt of an ultrasonic signal reflected from a particular flaw or other abnormality provides information about the flaw or abnormality. Thus, flaws, abnormalities, or other deviations from the material are detected and can be measured. Prior art uses of ultrasonic inspection have utilized the receiving transducer to receive sound by placing the transmitting and receiving elements generally facing one another and measuring signal loss due to the blockage of part of the sound wave before being received by the receiving transducer.

The primary advantage of a pitch-catch configuration versus a pulse-echo configuration is found when analyzing material with a low velocity that tends to be very attenuative. When using ultrasonics to test these types of materials, extra gain in the ultrasonic signal must be applied to adequately penetrate the low velocity, highly attenuative material. Unfortunately, problems can occur when the gain is raised to higher levels. A problem with the higher gain comes in the form of increased wedge and material noise. Thus, if a pulse-echo configuration is used as opposed to a pitch-catch configuration, the electronic probe can receive noise caused by reflection of the ultrasonic waves from the wedge itself or other variables not present in a pitch-catch configuration. Thus, in order to reduce the noise level, a pitch-catch configuration is utilized because it only receives the ultrasonic responses from the material and not from the wedge itself.

In any automatic ultrasonic flaw detection system, a major capital cost outlay is the area of the system's electronics for the flaw detection signal processing. The number of channels of a particular system will determine the number of transducer probes from which it can process signals. In order for an automated system to operate at high speeds, a wide scanning width is needed. This can be achieved by using large area single element probes for each channel of electronics, but the decrease in resolution of these larger probes often mandates smaller probes with a decreased inspection scan width. As a result, this increases the number of channels that a system will require for a given scan width.

In the past, various patents have issued relating to ultrasonic inspection devices and techniques. For example, U.S. Pat. No. 4,305,297, issued on Dec. 15, 1981, to Ries et al. teaches ultrasonic test equipment for testing the welding seam on a thick wall. This includes transducers arranged in tandem and along the welding seam. In this invention, a tandem pair of transducers scans for defects or abnormalities in the material. In addition, a third transducer is configured to capture data related to flaws and abnormalities in the material.

U.S. Pat. No. 4,522,064, issued on Jun. 11, 1985, to J. D. McMillan provides an ultrasonic method and apparatus for determining the depth of cracks in a pipe or conduit. This apparatus includes a transmitting transducer and a receiving transducer which are placed on the outside surface of the pipe. The transmitting transducer is energized to direct a shear wave beam of ultrasonic energy at the crack so as to generate a complex reflected wave front from the crack. This wave front contains the information as to the size of the crack in relation to the wall thickness. The receiving transducer is moved relative to the transmitting transducer until a peak or maximum amplitude reading is found.

U.S. Pat. No. 4,523,468, issued on Jun. 18, 1985, to Derkacs et al. provides a phased array inspection of cylindrical objects. A first array of ultrasonic transducers transmits ultrasonic shear waves circumferentially around an examined cylindrical object. A second array transmits ultrasonic shear waves axially along the examined object. Triggering pulses from a triggering amplifier are switched by a multiplexer to each individual transducer of the first and second arrays. As one of the transducers assumes the role of a transmitting transducer and transmits an ultrasonic wave, the other transducers of the first and second arrays assume a receiving mode to receive reflected ultrasonic components, i.e. a pitch-catch setup.

U.S. Pat. No. 4,641,531, issued on Feb. 10, 1987, to Reeves et al. describes an ultrasonic inspection apparatus for locating multiple defects in wall tubing. A plurality of transducers are arranged in mated pairs, each of the pairs including a sender element for transmitting an ultrasonic shear wave and a receiver element for receiving a reflected ultrasonic wave component from the tubular goods being inspected. Each sender element is a point focus transducer having sufficiently high resolution to maintain detectability of defects in the tubular goods.

U.S. Pat. No. 5,165,280, issued on Nov. 24, 1992, to Sternberg et al. provides a device for testing oblong objects through the use of ultrasonic waves. A transmitting ultrasonic transducer generates ultrasonic waves that are acoustically irradiated into the respective object via a coupling medium. At least three ultrasonic transducers are arranged in a row next to one another along the line. The transducers are aligned in an array wherein the outer transducers are set to receive the ultrasonic signals from the central transducer. The line array is inclined along the longitudinal axis of the object by an angle which is between zero degrees and forty-five degrees.

U.S. Pat. No. 5,189,915, issued on Mar. 2, 1993, to Reinhart et al. shows a single mode ultrasonic inspection method and apparatus. This is adapted to utilize both pitch/catch and pulse/echo information obtained by using a single mode of wave propagation. The apparatus includes an ultrasonic signal transmitting assembly, a signal receiving assembly, a positioning mechanism, and an arrangement for recording the information received by the signal receiving assembly. The transmitting assembly includes at least one source transducer for transmitting shear mode ultrasonic search signals into the mass of the object to be inspected. The signal receiving assembly receives shear mode ultrasonic signals that are produced as the ultrasonic search signals encounter discontinuities in the mass of the object being inspected. The signal receiving assembly also receives shear mode ultrasonic echo signals that are directed back to a first source transducer.

U.S. Pat. No. 5,431,054, issued on Jul. 11, 1995, to Reeves et al. discloses an ultrasonic flaw detection device including a transmitting ultrasonic transducer for producing multiple shear wave skips between inner and outer surfaces of a test object. It includes a plurality of receiving transducers positioned ahead of and parallel to at generally the same incident angle as the transmitting ultrasonic transducer. The device also includes a processor. The receiving transducers serve to receive energy of the shear wave as reflected from discontinuities or flaws in the object. Each of the receiving transducers is electronically isolated from the other receiving transducers. The receiving transducers are connected to a single channel of the processor. A fixture is provided having a first opening for detachably receiving the transmitting ultrasonic transducer and a plurality of receiving openers receiving the receiving transducers therein.

U.S. Pat. No. 6,736,011, issued on May 18, 2004, to Zayicek et al. discloses a method of ultrasonically inspecting an area around a disk bore and a keyway on a shrunk-on steam turbine disk that is attached to a rotor. The method includes placing one or more phased array ultrasonic probes on at least one face of the disk across from the keyway area without disassembling the disk from the rotor. The array then transmits ultrasonic energy in the form of one or more beams from one or more ultrasonic probes to scan along the disk bore and keyway area. Thus, flaws are detected and the waves that are reflected and diffracted from the flaws in the disk bore and keyway area are used to simultaneously reconstruct an image of the disk bore and keyway area. Thus, the image is used to detect and locate defects within the disk bore and keyway area.

U.S. Pat. No. 7,328,619, issued Feb. 12, 2008, to Moles et al. discloses an ultrasonic probe suited for testing the integrity of sheet metal surfaces around fastener openings. The probe uses means to center the probe over the opening including a mechanical centering rod and an electronic display. Once positioned within tolerance limits, phased array ultrasonic beams search for defects within the metal surfaces, allowing for residual offsets in the centering of the probe.

U.S. Pat. No. 7,428,842, issued Sep. 30, 2008, to Fair et al., discloses a phased array ultrasonic testing system for examining turbine disc bores and blade attachments for discontinuities, such as stress corrosion cracking. The system includes a control system with a computer and a controller for programming, emitting, and steering an ultrasonic beam via at least one two-dimensional phased array probe, thereby precisely inspecting the area of interest while simultaneously accommodating complex geometry of the disc or blade attachment. Computer control of the beam permits the number of inspection locations and the number of different probe wedges to be reduced.

U.S. Pat. No. 7,624,651, issued on Dec. 1, 2009, to Fernald et al. discloses and teaches an apparatus for damping an undesired component of an ultrasonic signal. The apparatus includes a sensor affixed to a pipe. The sensor includes a transmitter and a receiver. The transmitted ultrasonic signal includes a structural component propagating through the pipe and a fluid component propagating through a flow in the pipe. The receiver receives one of the transmitted components. The apparatus includes a damping structure. The damping structure dampens the structural component of the ultrasonic signal to impede propagation of the structural component to the receiver. The damping structure includes one of a housing secured to the pipe to modify ultrasonic vibrational characteristics thereof, a plurality of film assemblies including a tunable circuit to attenuate structural vibration of the pipe, and a plurality of blocks affixed to the pipe to either reflect or propagates through the blocks, the undesired structural component of the ultrasonic signal A significant problem in each of these prior art patents is present. The problem, inherent in phased array non-destructive testing, is the inability to scan directly under the surface of the material being scanned with a stationary probe. Because the phased array transducer, or any other non-destructive testing device, must rest on top of the material being scanned, there is an inability to scan within a certain angle from the surface of the material. In order to detect flaws near the surface of the material, the probe must be indexed (moved) in order for the ultrasonic waves to contact and thus detect the near-surface flaw. Near a joint where the probe cannot pass directly over the flaw, the only way a flaw can be detected is with a bounced beam. The ultrasonic beam is sent down into the material and bounced off the other wall back toward the surface upon which the device is resting. This way, the beam can detect the flaw, but only because the beam has already traveled the full thickness of the material and been reflected. Due to the reflection, the beam has become weakened, thus producing a much weaker signal. Thus, there exist places where a flaw can exist but cannot be detected without a reflected beam. Such a flaw is represented in FIG. 9. The three flaws in the material, each represented by a dot, are searched for by the phased array detector. However, as seen in the diagram, the prior art detector is unable to sweep the ultrasonic waves at an angle high enough to detect the topmost flaw, closest to the surface. Because of the nature of the wedge material and angle, the topmost flaw remains undetected by known ultrasonic phased array non-destructive testing. This is a problem because known techniques of non-destructive, phased array testing can miss flaws in materials because of the difficulty in sweeping the beam at such a high angle. Thus, there is a need for an apparatus and method capable of detecting flaws near the surface of the material being tested. Further, there is a need for an apparatus and method of testing that can utilize a phased array and sweep the beam at higher angles than are possible with current technology. The present invention fulfills these needs and solves these problems.

Thus, it is an object of the present invention to overcome the limitations found in the prior art and known apparatuses and methods used for non-destructive testing of materials with phased-arrays. It is a further object of the present invention to provide an ultrasonic detection system that can increase the effective depth coverage without a significant loss of resolution. It is a still further object of the present invention to provide an ultrasonic detection system that can increase the effective angle of sweeping of the ultrasonic waves without increasing the sound path of the ultrasonic waves. It is still a further object of the present invention to provide an ultrasonic inspection system that satisfies the goals and overcomes the problems in the prior art while still remaining easy to manufacture, easy to use, relatively inexpensive, and very accurate. The present invention achieves all of these goals and these and other objects and advantages of the present invention will become apparent from a reading of the attached specification and appended claims.

BRIEF SUMMARY OF THE INVENTION

The present invention is generally directed to a novel method and apparatus for non-destructive testing utilizing ultrasonic waves. In particular, the present invention is directed to a method and apparatus for non-destructive testing of material constructed of high density polyethylene. The present invention is directed to and includes an ultrasonic phased array wedge. The novel wedge is designed to accommodate a linear phased array transducer. The novel wedge is designed to contain a liquid with particular acoustic velocity characteristics. The present invention used in a preferred embodiment includes two wedges, constructed as mirror images and adjoined to each other with a separator, the two wedges each having an electronic probe configured to broadcast and receive ultrasonic waves respectively, in a pitch-catch configuration. The wedges are angled such that the resultant refraction of the ultrasonic soundwaves allows one to detect near-surface flaws without moving the wedges where with known wedge design one would have to move the wedge unit in order to detect the near-surface flaws.

The present invention is further directed to a wedge for non-destructive testing utilizing ultrasonic waves in a phased array. The wedge includes a housing with a ramp surface and a bottom opening, the ramp surface also including a top opening. The wedge also has a liquid column extending downwardly from the top opening to the bottom opening. Further, the wedge includes attachment means adapted to accept an electronic probe. The ramp surface slopes upwardly at an angle along the length or longitudinal axis of the wedge.

The present invention is further directed to a wedge wherein the housing includes a base, a front side, a back side, a first side, a second side, and a top surface. The wedge also has a ramp surface extending from the front side to the top surface.

The present invention is also directed to a wedge that includes a membrane attached to the base and adapted to cover the bottom opening. This membrane seals the liquid column and keeps the liquid from escaping the liquid column. The membrane also can flex and provides a further means of coupling the liquid in the liquid column to the material being analyzed.

The present invention is further directed to a wedge that includes a liquid inlet port and a screw. The screw can be a pin, plunger or conventional screw. The pin, plunger, or conventional screw is adapted to ingress or egress the wedge housing. This allows increasing or decreasing the volume of said liquid column and, therefore, increasing or decreasing the pressure in said liquid column.

The present invention is also contemplated to have a mounting port adapted to secure the wedge during automated use. The mounting port can support the wedge on any number of mounts or instrumentation.

The invention also includes an o-ring adapted to fit around the top opening. The o-ring provides a liquid tight engagement between the liquid column and the electronic probe. Thus, when the electronic probe is attached to the wedge, the liquid column can be filled with liquid so that no air pockets remain and the space inside the liquid column is completely filled with liquid.

Moreover, the present invention is still further directed to a wedge wherein the base is concave or convex to complement the shape of the material being analyzed. Thus, for applications involving the testing of pipes, the base of the wedge can be concave to fit around the circumference of the pipe.

The present invention contemplates a wedge wherein the angle along the longitudinal axis is from 0 degrees to 90 degrees.

Still further, the present invention is also directed to a wedge that includes irrigation ports on the housing. The wedge also has a reservoir inside the housing, separate from the liquid column, whereby liquid can flow through the irrigation ports and into and out of the reservoir. The reservoir can be closed or open, thereby allowing liquid to flow out of the wedge between the wedge and the surface of the material being tested. This aids in coupling the wedge to the surface of the material.

The present invention is still further directed to an apparatus for non-destructive testing utilizing ultrasonic waves in a phased array. The apparatus includes a wedge. The wedge has a housing defining a ramp surface and a bottom opening. The wedge's ramp surface defines a top opening and slopes at an angle along the length or longitudinal axis. The wedge has a liquid column extending downwardly from the top opening to the bottom opening and has attachment means adapted to accept an electronic probe. The apparatus also has a second wedge. The second wedge includes a housing defining a ramp surface and a bottom opening. The second wedge's ramp surface defines a top opening and slopes at an angle along the longitudinal axis like the first wedge. The second wedge also has a liquid column extending downwardly from its top opening to its bottom opening. The second wedge's ramp surface slopes at an angle along the length or longitudinal axis. The second wedge also includes attachment means adapted to accept an electronic probe.

The invention further contemplates an apparatus wherein the first wedge and the second wedge are abutted against opposite sides of a dampener separating the first wedge from the second wedge. The dampener can be comprised of any material sufficient to dampen the echoes or noise caused by ultrasonic wave reflecting off of the wedge itself. Typically this material can be cork.

The present invention further contemplates an apparatus wherein the ramp surface on the first wedge is sloped at an angle along the width or secondary axis toward the second wedge. The ramp surface on the second wedge is sloped at an angle along its width or secondary axis toward the first wedge. Thus, the wedges slightly point at each other.

The present invention also contemplates and is directed to an apparatus wherein the angle of the ramp surfaces along the longitudinal axis is from 0 degrees to less than 90 degrees and the angle along the secondary axis is from 0 degrees to less than 90 degrees. Still further, the apparatus may have the angle of the ramp surfaces along the longitudinal axis from 20 degrees to 40 degrees and the angle along the secondary axis from 0 degrees to 20 degrees. In a particular embodiment to analyze a particular material, the present invention includes an apparatus wherein the angle of the ramp surfaces along the longitudinal axis is approximately 29 degrees and the angle along the secondary axis is approximately 4 degrees.

The present invention further contemplates and is directed to an apparatus including a base plate wherein the first wedge is affixed to the base plate and the second wedge is affixed to the base plate along the longitudinal axis of the first wedge, directly behind the first wedge. Thus, the wedges are aligned in tandem on the base. Further, the apparatus includes slots in the base plate for affixing the first and second wedges, such that by moving the first and second wedges in the slots, the distance between the first wedge and the second wedge can be varied.

The present invention is also directed to a method of non-destructive testing of materials including the steps of providing an apparatus including a wedge having a housing defining a ramp surface and a bottom opening, where the ramp surface defines a top opening. The provided wedge also has a liquid column extending downwardly from the top opening to the bottom opening. The provided wedge further has attachment means adapted to accept an electronic probe, and the wedge's ramp surface slopes upwardly at an angle. The method further includes the steps of placing the wedge on the surface of a material to be tested and sending ultrasonic waves via a phased array from the wedge into the material. The method also includes the step of analyzing the ultrasonic waves reflected from the material.

The method according to the present invention further contemplates providing an apparatus having a first wedge and a second wedge that are configured in a pitch-catch configuration. The method includes placing the apparatus on to the surface of the material to be analyzed and sending ultrasonic waves via a phased array into the material. The method further includes the step of analyzing the ultrasonic waves reflected from the material.

DETAILED DESCRIPTION OF THE INVENTION

The present invention will be described herein as it relates to the non-destructive testing of high density polyethylene pipes and joints. Those skilled in the art will quickly realize that the techniques and apparatus described herein can also be used for non-destructive testing on a wide range of materials and objects. Thus, the principle target of inspection, high density polyethylene materials, should not be read as a limitation on the applicability of the present invention.

Figure 1:
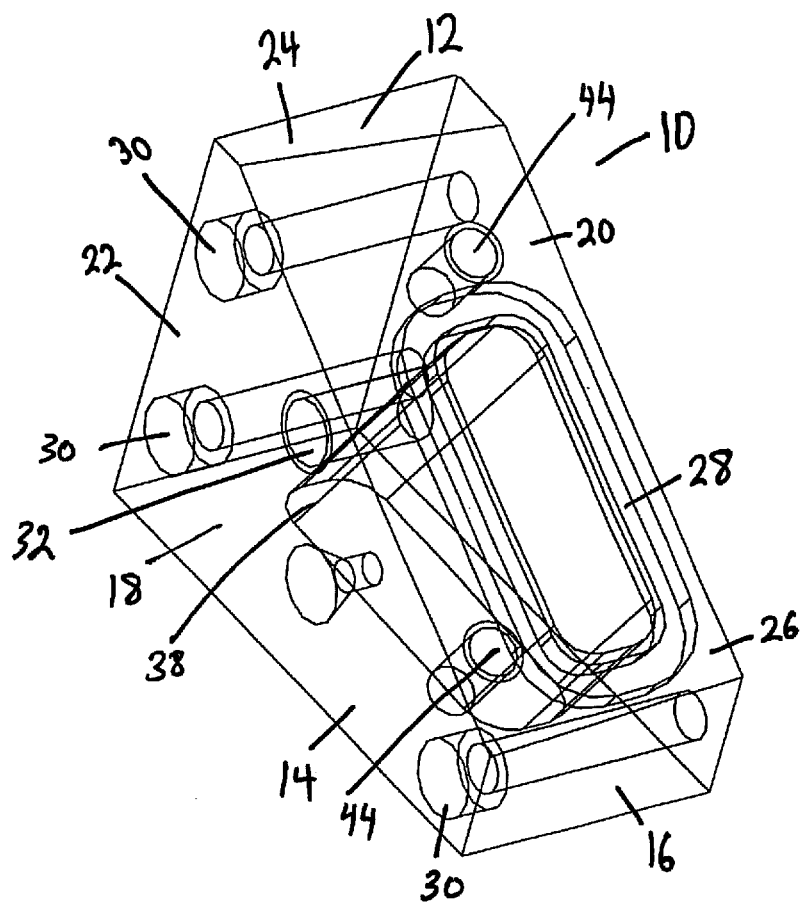
FIG. 1 is plan view of the present invention.

Referring now to FIG. 1, the wedge 10 is illustrated in its simplest form as a wedge housing 12 that defines a cavity therein. The wedge housing 12 has a base 14, a front side 16, a first side 18, a second side 20, a back side 22, a top surface 24, and a ramp surface 26 that spans between the front side 16 and the top surface 24. The ramp surface 26 defines a top opening 28 generally in a rectangle with rounded corners shape that provides access to the interior of the wedge 10.

The first side 18 of the wedge housing 12 defines a plurality of openings 30 to accommodate attachment means that enable the wedge 10 to attach to a mirror image wedge 10 in a preferred embodiment. Such attachment devices can be any known attachment means such as screws, pins, rods, etc. The first side 18 further defines a liquid inlet port 32 whereby liquid can be fed into the wedge 10. A screw 34 (shown in FIG. 2) or plug is placed into the inlet port 32 to prevent liquid from flowing out of the wedge 10. An o-ring 36 (shown in FIG. 3) is fitted onto the screw 34 such that the o-ring 36 contacts the screw 34 and the first side 18 to ensure that no liquid can leak from the wedge 10. It should be appreciated by those skilled in the art that the liquid inlet port 32 can be located on the second side 20 (as a mirror image) or any other place on the wedge housing 12 that provides access to the interior of the wedge 10.

Figure 2:
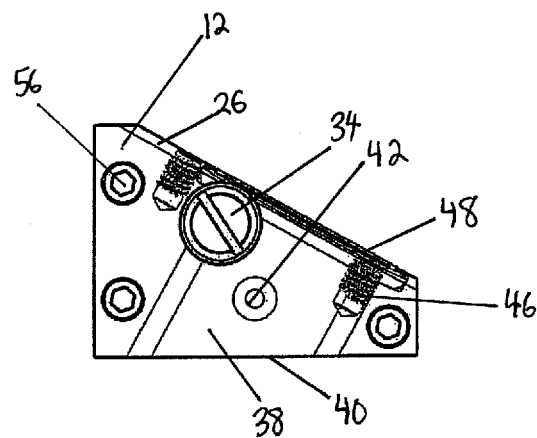
FIG. 2 is a side view of the present invention.

Referring now to FIG. 2, a liquid column 38 is shown. The liquid column 38 is defined by the wedge housing's 12 cavity and corresponds to the shape defined by the rectangular opening 28. The liquid column 38 is further defined by a membrane 40 (not shown) located on the base 14 defining the bottom of the liquid column 38. The membrane 40 can be manufactured from a variety of materials, however, the membrane 40 must be capable of conducting ultrasonic waves and deforming under pressure from the liquid in the liquid column 38. In a preferred embodiment, the membrane 40 is manufactured from a generally thin, flexible material. The screw 34 holding the liquid inside of the liquid column 38 can be designed to seal the liquid column 38 against leaks yet also provide a mechanism by which the screw 34 can continue to rotate and exert pressure on the liquid contained within the liquid column 38. The pressure generated by the screw 34 will force the liquid to exert pressure against the membrane 40 and deform the membrane 40 outwardly from the wedge 10. Thus, the membrane 40 can be pressed tightly against the surface of the material being examined. This allows the liquid in the liquid column 38 to be contained while allowing a bulge that improves the amount of ultrasonic energy (through coupling) that enters the material being tested. As can be seen from FIG. 2, the inlet port 32 should be located above the membrane 40 substantially near the top of the liquid column 38 for ease in filling the liquid column 38 with liquid.

Also included on the wedge housing 12 is a mounting port 42. The mounting port 42 is located on the first side 18 and can be strategically placed on the first side 18 to provide access to a mounting bracket (not shown) that will secure the wedge 10 during use. The mounting port 42 advantageously is constructed to define a threaded hole for insertion by a mounting screw or other known mounting device. As can be appreciated by those skilled in the art, the mounting port 42 can be designed to allow securing by a pin in order to allow the wedge 10 to rotate on the pin at the mounting port 42. This will allow the wedge 10 to rotate around the material being tested while remaining secured to the instrumentation or other supporting structure.

The ramp surface 26 of the wedge housing 12 further defines a plurality of attachment ports 44 that are configured to accept helical screws 46 or other attachment means to secure an electronic probe (not shown) to the wedge 10. The electronic probe must be securely attached to the wedge 10 to ensure that stray vibrations resulting from loose fittings are reduced and do not interfere with the measurements of the ultrasonic waves. In addition, the attachment means to secure the electronic probe to the wedge 10 must be secure enough and maintain contact between the electronic probe and the wedge 10 such that no liquid can leak out the top of the liquid column 38. In operation, the electronic probe and the liquid in the liquid column 38 must remain in continual contact in order for transmission of the ultrasonic waves. Any leak of liquid can cause interference and disrupt the analytical process.

Figure 3:
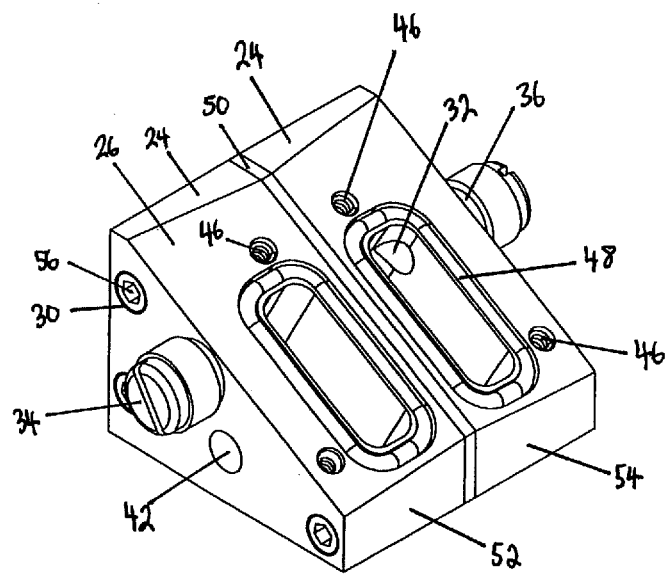
FIG. 3 is a plan view of a preferred embodiment of the present invention used in mirror image configuration.
Figure 4:
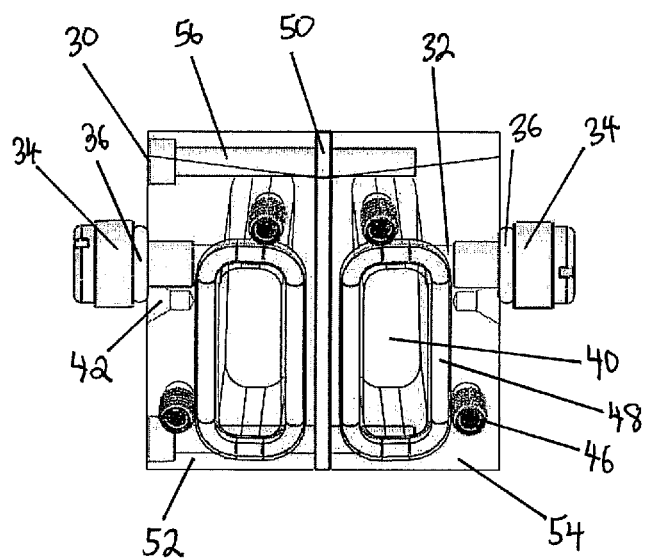
FIG. 4 is a top view of a preferred embodiment of the present invention used in a mirror image configuration.

Referring now to FIGS. 3 and 4 which show a preferred embodiment of the present invention, a large o-ring 48 is shown surrounding the rectangular opening 28 defined by the wedge housing 12 on the ramp surface 26. The large o-ring 48 is configured to form a liquid tight seal between the electronic probe (not shown) and the wedge 10 such that no liquid can escape from the liquid column 38 when the electronic probe is attached. As the electronic probe is secured to the wedge housing 12 by the helical screws 46, the large o-ring 48 is squeezed between the electronic probe and the wedge ramp surface 26. Thus, the large o-ring 48 provides a liquid tight seal between the electronic probe and the liquid column 38.

Still referring to FIG. 3, two wedges 10 are configured to be mirror images of one another. A cork dampener 50 is placed adjacent to the inner side of each of the wedges 10. For ease of reference, the wedge 10 on the left shall be referred to as the left wedge 52 and the wedge 10 on the right side shall be referred to as the right wedge 54. The cork dampener 50 is placed between the left wedge 52 and the right wedge 54 and configured to substantially conform to the shape of the left wedge 52 and the right wedge 54.

The left wedge 52 is configured with the openings 30 to accommodate a securing screw 56 or other fastener. The securing screw 56 passes through the left wedge 52, into and through the cork dampener 50, and into the right wedge 54. The right wedge 54 must be configured with an opening 30 adapted to receive a securing screw 56 or other fastener so that the left wedge 52, cork dampener 50, and right wedge 54 are securely attached to each other. The cork dampener 50 is utilized as a sound dampener that will eliminate echoes, cross talk, and other interference within the apparatus. The left wedge 52 and the right wedge 54 could echo between each other in the absence of the cork dampener 50. Such echoes could interfere with the collection of ultrasonic wave data. As can be appreciated by those skilled in the art, the cork dampener 50 could be replaced by another material as long as the alternate material effectively reduced echoes between the left wedge 52 and the right wedge 54.

Still referring to FIG. 3, it can be seen that the ramp surface 26 on the left wedge 52 and the right wedge 54 slopes upwardly from the front side 16 to the back side 22 along the primary axis (length) of the wedge 10. The ramp surface 26 slopes upwardly at an angle greater than 0° and less than 90°. In a preferred embodiment for testing high density polyethylene, the angle is approximately 29°. In addition to the ramp surface 26 sloping upwardly from the front side 16 to the back side 22, the ramp surface 26 slopes upwardly from the outer edge (first side 18) toward the inner edge (second side 20) along the secondary axis (the width) adjacent to the cork dampener 50. The ramp surface 26 slopes upwardly toward the cork dampener 50 at an angle greater than 0° less than 90°. In a preferred embodiment for testing high density polyethylene piping, the angle is approximately 4°.

In operation, two electronic probes are attached to the wedges 10, one to the left wedge 52 and one to the right wedge 54. The electronic probes are configured through software or other known means to broadcast and receive ultrasonic waves. In a preferred embodiment, the probes are configured in a pitch-catch configuration wherein the electronic probe attached to the left wedge 52 broadcasts the ultrasonic waves and the electronic probe attached to the right wedge 54 is configured to receive the ultrasonic waves. As one can readily appreciate, this configuration can be reversed.

Water is pumped into the liquid column 38 such that the entire cavity defined by the liquid column 38, membrane 40, and surface of the electronic probe is filled with water. The water in the liquid column 38 causes the ultrasonic waves broadcast by the electronic probe to refract at the interface of the liquid in the liquid column 38 and the material to be tested. The membrane 40 is preferably manufactured at such a low thickness that it will not impede the transmission of the ultrasonic waves. In a preferred embodiment, the membrane 40 is less than one wavelength thick so as to not be ultrasonically detectable.

The ultrasonic waves refract at the intersection of the water or other liquid in the liquid column 38 and the material being scanned due to the difference in the acoustic velocities of the respective materials. Water has a much slower acoustic velocity than the typical material being tested. For example, water's longitudinal velocity is approximately 0.058 inches per microsecond while high density polyethylene has a longitudinal velocity of approximately 0.092 inches per microsecond. Thus, when the ultrasonic waves transition from the slower water into the faster high density polyethylene, refraction occurs. It should be appreciated by those skilled in the art that this ability to refract can vary depending on the acoustic characteristics of the liquid in the liquid column 38 and the material being analyzed.

Figure 9:
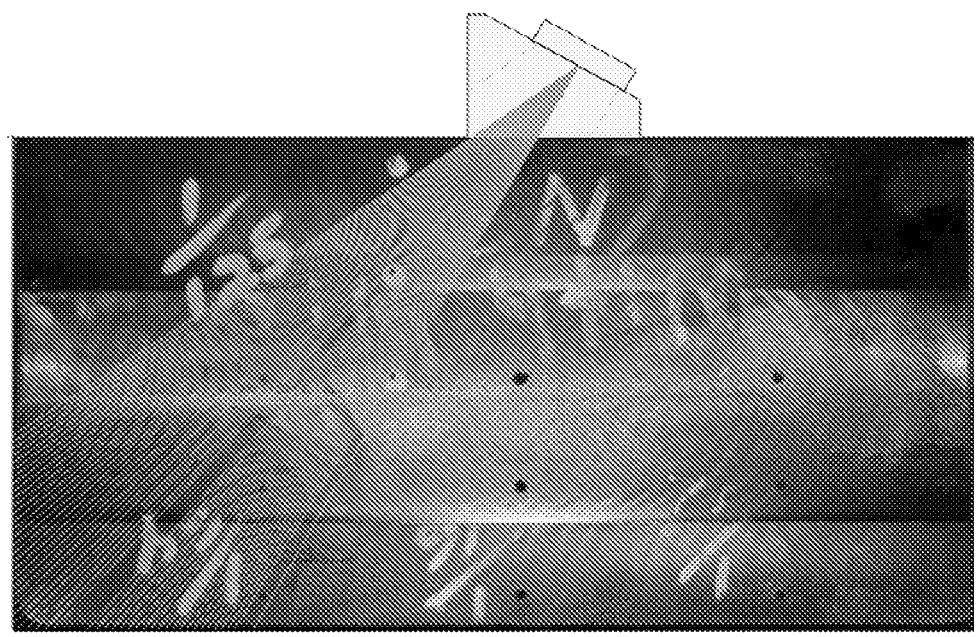
FIG. 9 is a photograph of a detector according to the prior art.

The refraction allows the sweeping of the resultant beams such that an increased area of the material is scanned. FIG. 9 represents a typical scan by a prior art ultrasonic phased array using a standard wedge.

The three flaws in the material, each represented by a dot, are searched for by the prior art phased array detector. However, as seen in the illustration, the detector is unable to sweep the ultrasonic waves at an angle high enough to detect the topmost flaw, closest to the surface. Because of the nature of the wedge material and angle of the prior art wedge, the topmost flaw remains undetected by known ultrasonic phased array non-destructive testing.

Figure 10:
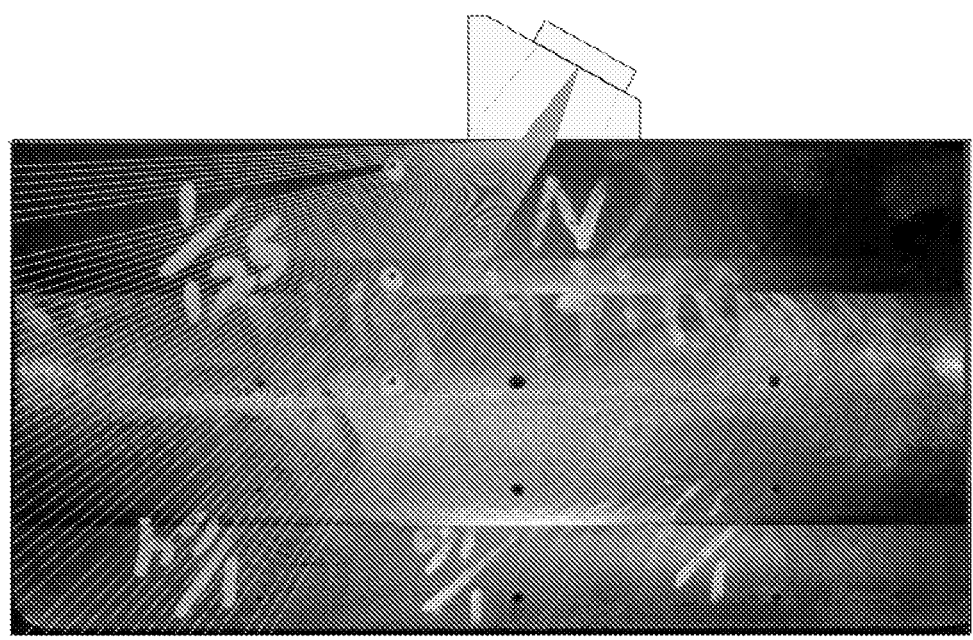
FIG. 10 is a photograph of a detector according to the present invention.

In contrast, the use of water in the liquid column 38, and the use of precise angles of the invented wedge 10, refracts the ultrasonic waves such that the beam can be swept through and cover a greater area of the subject material. As shown in FIG. 10, the use of water and precise angles allow the detection of the flaw closest to the surface of the material.

As can be readily seen, the uppermost flaw is easily detected by the present wedge 10 due to the use of water in the liquid column 38 and the precise angles. The angle of the ramp surface 26, or "roof angle," combined with the ability of the water in the liquid column 38 to refract the ultrasonic waves allows one to sweep the beam over an increased depth inside the material being examined. Thus, in the illustration above, the uppermost flaw is detected where it would be missed by a prior art wedge.

The advantages of the pitch-catch design is further complemented and enhanced by changing the roof angles and resulting refraction to optimize focusing in low velocity materials. The wedge 10 is designed to include a liquid column 38 that can be filled with a suitable liquid. As different liquids have different refractive properties, one can choose an appropriate liquid filler based upon the desired refractive angle or other pertinent factors. In a preferred embodiment for analyzing high density polyethylene pipe, water is used to fill the liquid column 38. The present invention is able to achieve good results and overcome the problems in the prior art by attaining an improved refraction using water to fill the liquid column 38. The liquid inlet port 32, located on the side of the wedge 10, is necessary in order to fill the liquid column 38 with an acceptable liquid, in this case water. As discussed earlier, refraction occurs because water has a much slower longitudinal velocity (0.058 in/µs) than that of low velocity materials (for example, high-density polyethylene has a longitudinal velocity of 0.092 in/µs). A further consideration in determining the optimum liquid to use in the liquid column 38 is that the extent of the refraction of the ultrasonic waves depends heavily on the acoustic velocity of the test material being applied. Thus, depending on the material of the item to be scanned, alternative liquids can be utilized.

The wedge 10 is specifically designed to have an identifiable angle along the primary axis (defined as the length of the wedge 10). This angle, representing the slope of the ramp surface 26 of the wedge 10, is determined by the desired refractory angle, which is in turn dependant on the material being analyzed. In a preferred embodiment, the angle along the primary axis is 29°. An angle of 29° when used in conjunction with water in the liquid column 38 produces a refracted primary angle of approximately 50°. Again, this angle can vary slightly depending on the exact longitudinal velocity of the test material.

Figure 5:
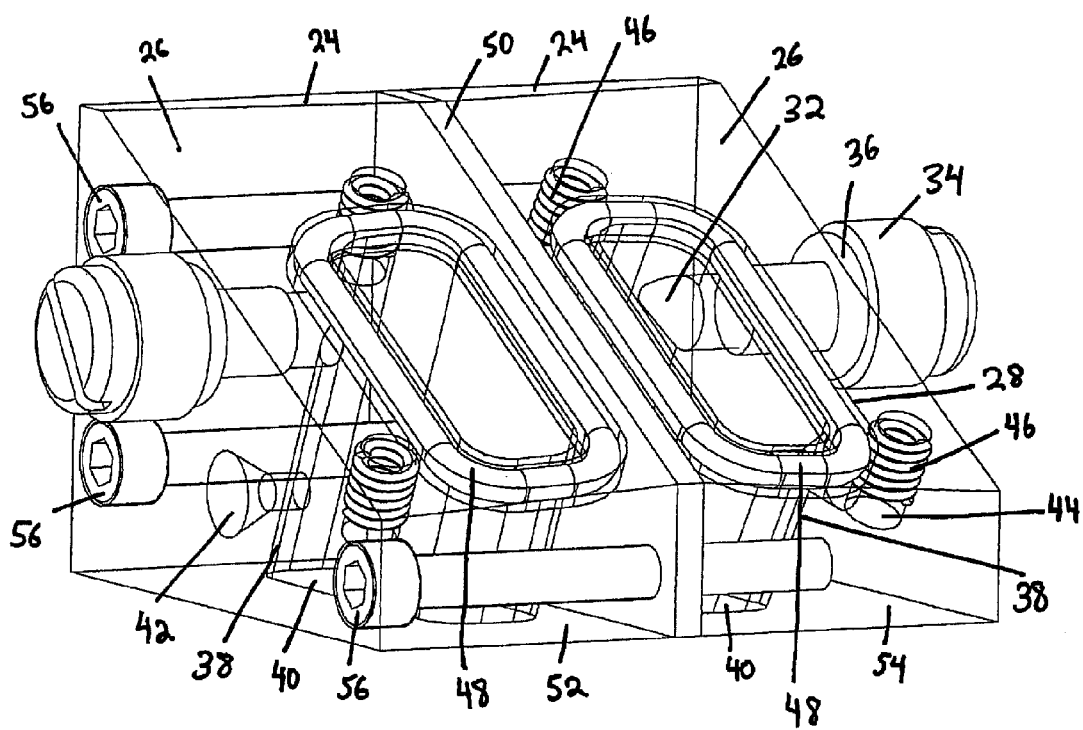
FIG. 5 is a plan view of a preferred embodiment of the present invention used in a mirror image configuration.

Referring now to FIG. 5, the angles of the pitch-catch wedge configuration are easily seen. In addition to the angle along the primary axis being important, the angle along the secondary axis (the width) of the wedge 10 is also important. The angle of slope of the ramp surface 26 along the secondary axis enables the wedges 10 to point towards each other, facilitating the pitch-catch setup. As seen in FIG. 5, the mirror image wedges 10 are configured such that the electronic probes are angled along the wedge's 10 secondary axis such that the electronic probes will be slightly pointed toward each other. The angle at which the wedges 10 point toward each other is determined by the desired focal point of the sweeping beams. Thus, the angle may change depending on the identity of the material being analyzed and the depth at which the focal point is desired. Generally, the angle will be greater than or equal to 0° up to less than 90°. For testing of high density polyethylene at a known thickness in a preferred embodiment, the angle is approximately 4° in order to optimize the focusing capabilities of the emitted ultrasonic beams along a defined offset in front of the wedge 10.

Figure 6:
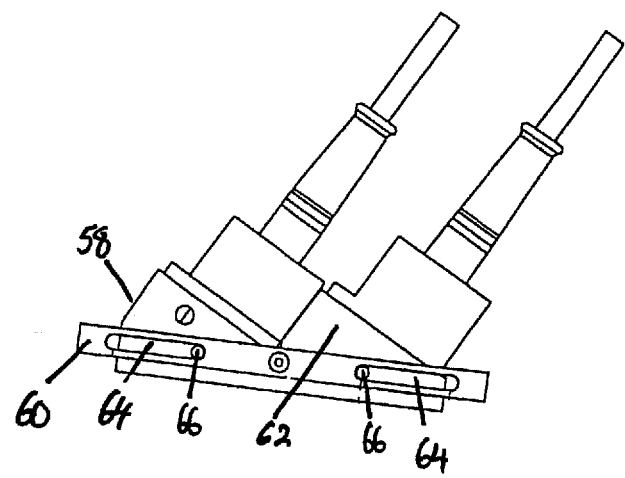
FIG. 6 is a side view of an alternative embodiment of the present invention used in tandem configuration.

Referring now to FIG. 6, an alternative embodiment of the present invention is shown. In this configuration, two wedges 10 are set up in tandem. A front wedge 58 is secured to a base plate 60 through the mounting port 42 on the wedge 10. A rear wedge 62 is secured to the base plate 60 through the mounting port 42 on the wedge 10. The front wedge 58 and the rear wedge 62 may slide towards and away from each other by means of slots 64 in the base plate 60 in which a pin 66 secures the base plate 60 to the wedges 10 by means of the mounting ports 42. The pin 66 can be of a known configuration to allow one to tighten the wedges 10 to the base plate 60 such that the wedges 10 are unable to move. The front wedge 58 and the rear wedge 62 may touch or may be separated such that they do not abut each other. Further, a dampener (not shown) such as a piece of cork can be adapted to use between the front wedge 58 and the rear wedge 62.

Figure 7:
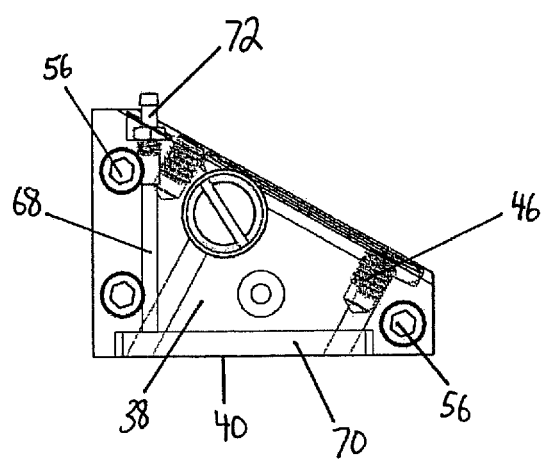
FIG. 7 is a side view of an alternative embodiment of the present invention.
Figure 8:
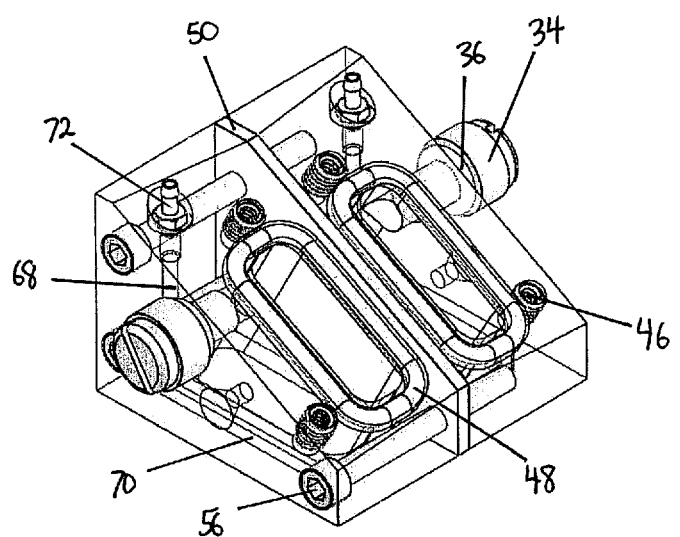
FIG. 8 is a plan view of an alternative embodiment of the present invention.

Referring now to FIGS. 7 and 8, a further embodiment of the present invention is shown. This embodiment of the wedge 10 is adapted to contain an irrigation system. The irrigation system has an irrigation pipe 68 running vertically from the top of the ramp surface 26 downwardly through the wedge 10 to just above the base 14. The irrigation pipe 68 terminates into a reservoir 70 that is integrally formed by the base 14 of the wedge 10. The reservoir 70 is designed to substantially wrap around the liquid column 38. The irrigation pipe 68 has at its top end means to attach to a source of liquid to be pumped into the irrigation pipe 68 and the reservoir 70. The attachment means is typically that of threaded grooves adapted to accept a barb 72. The barb 72 has grooves designed to screw into the top of the irrigation pipe 68 forming a liquid tight seal. The barb 72 is further adapted to attach to a hose, faucet, or other source of liquid. Liquid, typically water, is pumped into the barb 72 and down the irrigation pipe 68 into the reservoir 70. In operation, the wedge 10 is placed onto the surface of the material to examine and the liquid is pumped into the irrigation system. As the analysis of the material commences, the wedge 10 is slowly moved down the surface of the material being tested. The irrigation system allows liquid to be pumped into the wedge and to seep out around the interface of the wedge 10 with the material being analyzed. This has a coupling effect and aids in the measurement and detection of flaws. The liquid is pumped into the irrigation system at a rate such that the liquid slowly seeps out from under the wedge 10 between the base 14 of the wedge 10 and the material being examined. The irrigation system is independent from the liquid contained in the liquid column 38, and, in fact, different liquids can be used for either the liquid column 38 or the irrigation system depending on the desired results.

However, it has been found that it is possible to analyze materials without the use of a membrane 40 in the wedge 10. Scanning can be accomplished simply by continually pumping liquid into the liquid column 38 and allowing the liquid to seep out from the interface of the base 14 of the wedge 10 with the material being examined. The liquid couples together the wedge 10 and the material being examined. Thus, it is possible to integrate the irrigation system with the liquid column, if one desires to use the same liquid in the irrigation system that is being used in the liquid column 38. In this embodiment, the liquid would fill both the liquid column 38 and the irrigation system.

Currently, the present invention allows the easy detection of 0.008 in. diameter near-surface side-drilled holes in high density polyethylene material. As those skilled in the art will readily appreciate from the foregoing description and discussion, this confirms the improved refraction and volumetric coverage due to the novel wedge design. Additionally, when coupled with optimized electronic probe parameters, the specific angles aid in sweeping and focusing. This leads to improved resolution of clustered indications and flaws where known methods and devices would be unable to detect.

The foregoing discussion has been proffered as an exemplary description of preferred embodiments of the present invention. The description has discussed and illustrated how the present invention works and can be applied to and used for its intended purpose. It is the intention of the inventors to claim the present invention in its broadest sense, and not be limited to the exemplary facets discussed above. The invention in its broadest sense is encompassed by the following claims which should be understood in light of the foregoing discussion, but should not be limited by particular descriptions of preferred embodiments. Rather, the claims should be read to encompass the full scope of the invention as implicit from the description and disclosure provided herein.

We claim:

1. An apparatus for non-destructive testing utilizing ultrasonic waves in a phased array comprising:
   a first wedge and a second wedge;
   said first wedge including a housing defining a ramp surface and a bottom opening, said ramp surface defining a top opening and sloping at an angle from greater than 0 degrees to less than 90 degrees along the longitudinal axis, and sloping at an angle from 0 degrees to less than 90 degrees along a secondary axis toward said second wedge;
   a liquid column extending downwardly from said top opening to said bottom opening;
   attachment means adapted to accept an electronic probe;
   said second wedge including a housing defining a ramp surface and a bottom opening, said ramp surface defining a top opening and sloping at an angle from greater than 0 degrees to less than 90 degrees along the longitudinal axis, and sloping at an angle from 0 degrees to less than 90 degrees along a secondary axis toward said first wedge;
   a liquid column extending downwardly from said top opening to said bottom opening, said ramp surface sloping at an angle; and
   attachment means adapted to accept an electronic probe.

2. An apparatus according to claim 1 wherein the angle of said ramp surfaces along the longitudinal axis is from 20 degrees to 40 degrees and the angle along the secondary axis is from 0 degrees to 20 degrees.

3. An apparatus according to claim 1 wherein the angle of said ramp surfaces along the longitudinal axis is approximately 29 degrees and the angle along the secondary axis is approximately 4 degrees.

4. An apparatus for non-destructive testing utilizing ultrasonic waves in a phased array comprising:
   a first wedge and a second wedge;
   said first wedge including a housing defining a ramp surface and a bottom opening, said ramp surface defining a top opening and sloping at an angle from greater than 0 degrees to less than 90 degrees along the longitudinal axis, and sloping at an angle from 0 degrees to less than 90 degrees along a secondary axis toward said second wedge ;
   a liquid column extending downwardly from said top opening to said bottom opening;
   attachment means adapted to accept an electronic probe;
   said second wedge including a housing defining a ramp surface and a bottom opening, said ramp surface defining a top opening and sloping at an angle from greater than 0 degrees to less than 90 degrees along the longitudinal axis, and sloping at an angle from 0 degrees to less than 90 degrees along a secondary axis toward said first wedge;
   a liquid column extending downwardly from said top opening to said bottom opening, said ramp surface sloping at an angle;
   a base plate wherein said first wedge is affixed to said base plate and said second wedge is affixed to said base plate along the longitudinal axis of said first wedge, directly behind said first wedge; and
   attachment means adapted to accept an electronic probe.

5. An apparatus according to claim 4 further including slots in said base plate for affixing said first and second wedges, such that by moving said first and second wedges in said slots the distance between said first wedge and said second wedge can be varied.

* * * * *